(# United States Patent [19]

Manning

[11] 3,963,780
[45] June 15, 1976

[54] N,N'-DISUBSTITUTED-P-PHENYLENEDIAMINES

[75] Inventor: Robert E. Manning, Mountain Lakes, N.J.

[73] Assignee: Sandoz, Inc., E. Hanover, N.J.

[22] Filed: Feb. 14, 1974

[21] Appl. No.: 442,615

Related U.S. Application Data

[60] Division of Ser. No. 211,109, Dec. 22, 1971, Pat. No. 3,819,708, and a continuation-in-part of Ser. No. 118,517, Feb. 24, 1971, abandoned, and a continuation-in-part of Ser. No. 118,518, Feb. 24, 1971, abandoned.

[52] U.S. Cl.................. 260/570.8 R; 260/501.12; 260/501.2; 260/501.21; 260/573; 260/577; 424/316; 424/330
[51] Int. Cl.².......................................... C07C 87/29
[58] Field of Search................. 260/570.8, 570.8 R, 260/501.12, 501.2, 501.21; 424/330

[56] References Cited
OTHER PUBLICATIONS

Ashton et al., "Chemical Abstracts," vol. 52, pp. 9071–9072 (1958).
Ried et al. "Chemical Abstracts," vol. 53, pp. 1373–1374 (1959).
Matrick et al., "Chemical Abstracts," vol. 55, pp. 25924–25925 (1961).

*Primary Examiner*—R. V. Hines
*Attorney, Agent, or Firm*—Gerald D. Sharkin; Robert S. Honor

[57] ABSTRACT

N,N'-disubstituted-p-phenylenediamines, e.g., N-(3-isopropoxypropyl)-N'-(2-octyl)-p-phenylenediamine or N-phenethyl-N'-(2-octyl)-p-phenylenediamine, are prepared by condensing phenylenediamines with an alkyl carbonyl in the presence of a reducing catalyst, and are useful as hypolipidemic and anti-obesity agents.

4 Claims, No Drawings

N,N'-DISUBSTITUTED-P-PHENYLENEDIAMINES

This is a division of application Ser. No. 211,109, filed Dec. 22, 1971, and now U.S. Pat. No. 3,819,708.

This is a continuation-in-part of copending U.S. patent application, Ser. No. 118,518, filed Feb. 24, 1971 and Ser. No. 118,517, filed Feb. 24, 1971 and now both abandoned.

This invention relates to phenylenediamine derivatives useful as hypolipidemics and anti-obesity agents. In particular, this invention relates to N-phenalkyl or alkoxy alkyl-N'-alkyl-p-phenylenediamines, processes for their preparation and their use in pharmaceutical compositions.

The compounds of this invention may be represented by the following formula:

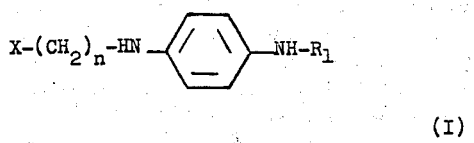

(I)

where
  $n$ is 2, 3, or 4
  X is phenyl or lower alkoxy, i.e., alkoxy having 1 to 4 carbon atoms, e.g., methoxy, ethoxy, isopropoxy and the like and
  $R_1$ is straight or branched chain alkyl having 5 to 11 carbon atoms, e.g., 2-heptyl, 2-octyl and the like; and pharmaceutically acceptable acid addition salts thereof.

The compounds of formula (I) having the formula:

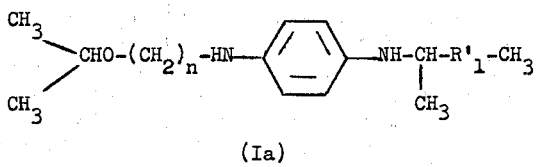

(Ia)

where $n$ is as defined above and R' is straight or branched chain alkyl having 4 to 7 carbon atoms and pharmaceutically acceptable acid addition salts thereof are preferred.

The compounds of formulas (I) and (Ia) may be prepared in accordance with the following process:

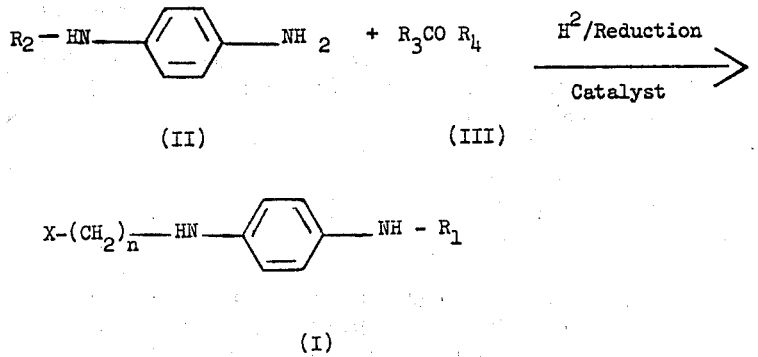

where
  $R_2$ represents $X-(CH_2)_n-$ or straight or branched chained alkyl having 5 to 11 carbon atoms and
  $R_3CO R_4$ is a straight or branched chained aldehyde or ketone having 5 to 11 carbon atoms or $X-(CH_2)_{n-1}-CHO$ where $n$, X and $R_1$ are defined above, provided that when $R_2$ is $X-(C_2)_n-$, $R_3COR_4$ is a straight or branched chained aldehyde or ketone having 5 to 11 carbon atoms and that when $R_2$ is straight or branched chained alkyl having 5 to 11 carbon atoms, $R_3COR_4$ is $X-(CH_2)_{n-1}-CHO$.

The compounds (I) are prepared by the reductive alkylation of a compound of formula (II) with a compound of formula (III). The preferred catalyst for the reductive alkylation is 5% platinum sulfide on carbon, although the particular reductive alkylation catalyst used is not critical. A solvent is not necessary in the process, but if desired, excess reagent (II) or (III) can be used, especially the carbonyl compound (III). Neither the temperature nor the pressure of the hydrogen employed in the reductive alkylation is critical. It is preferred, however, that the reaction be run at temperatures between about 120° to 200°C., especially between about 140° to 180°C. The preferred pressure range is between about 200 to 1200 psi, especially between about 400 to 700 psi. The time of the reaction is not critical, but it is preferred that the reaction be run for 1 to 10 hours, preferably 3 to 7 hours. The product is recovered by conventional techniques, e.g., extraction and recrystallization.

The compounds of formula (I) can also be prepared in accordance with the following reaction scheme:

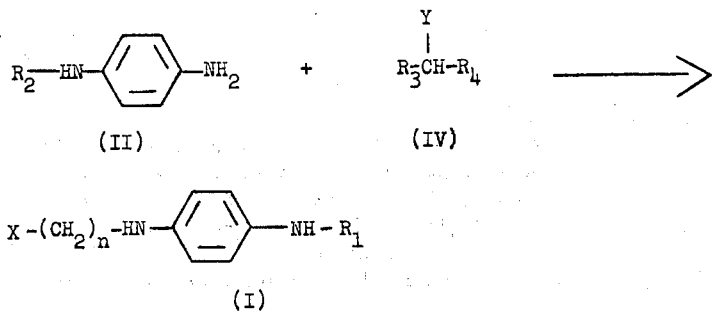

where
Y is halo having an atomic weight of about 35 to 80
$R_2$ is $X-(CH_2)_n-$ or straight or branched chain alkyl having 5 to 11 carbon atoms,

is $X-(CH_2)_{n-1}-CH_2Y$ is a straight or branched chain alkyl halide having 5 to 11 carbon atoms and $n$, X and $R_1$ are as set out above,
provided that when $R_2$ is $X-(CH_2)_n-$,

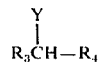

is a straight or branched chan alkyl halide having 5 to 11 carbon atoms or that when $R_2$ is straight or branched chain alkyl having 5 to 11 carbon atoms,

is $X-(CH_2)_{n-1}-CH_2Y$.

The compounds of formula (I) are prepared by treating a compound of formula (II) with a compound of formula (IV). The process is conveniently carried out in an inert organic solvent, such as dioxane, an alkanol of 1 to 6 carbon atoms, benzene or toluene, or in an excess of the halide of formula IV. Although the reaction temperature is not critical, the reaction is generally carried out at a temperature of from 10° to 100°C, preferably 40° to 70°C. The reaction is also conveniently carried out in the presence of an acid binding agent, such as a tertiary amine, e.g. triethylamine, or an inorganic base, preferably an alkali metal carbonate, e.g., sodium or potassium carbonate. The product may be recovered by conventional techniques, e.g. evaporation and extraction. The compounds of formula (II) in which $R_2$ is phenalkyl are novel and represent another aspect of this invention. The compounds may be prepared in accordance with the following process:

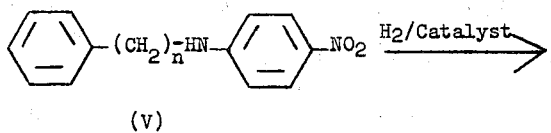

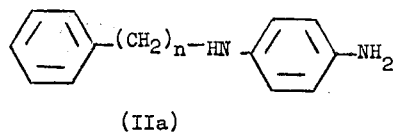

wherein $n$ is as defined above.

The compounds of formula (IIa) are prepared by reducing the compounds of formula (V) with hydrogen in the presence of a reduction catalyst and inert solvent. The particular catalyst used for the reduction is not critical but platinum or palladium, especially 10% palladium on carbon is preferred. The solvent used in the process can be any inert solvent but the lower alcohols, especially methanol and ethanol are preferred. Neither the temperature nor the pressure of the hydrogen employed in the reductive alkylation is not critical. It is preferred, however, that the reduction by run at temperatures between about 10° to 40°C., especially between about 20° to 30°C. The preferred pressure range is between about 1 to 50 atmospheres. The time of the reaction is not critical, but it is preferred that the reaction be run for 10 minutes to 4 hours, preferably 1 to 2 hours. The product is recovered by conventional techniques, e.g., recrystallization.

The compounds of formula (V) are also novel and are prepared in accordance with the following process:

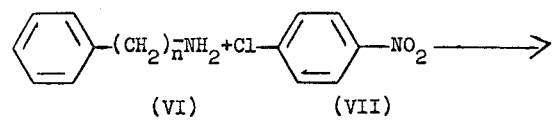

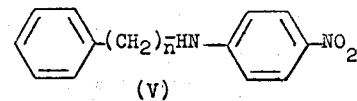

where $n$ is as defined above.

The compounds of formula (V) are prepared by treating a compound of formula (VI) with a compound of formula (VII) in a inert solvent. The inert solvents which can be used include dimethyl sulfoxide, dimethylamine, dimethylformamide or lower alkanols. The particular solvent used is not critical, but dimethyl sulfoxide is especially preferred. An excess of compound (VI) is usually added to remove the acid liberated during the reaction. Although the temperature at which the reaction is carried out is not critical, it is preferred that the reaction be run at temperatures between about 50° to 170°c., preferably 100° to 150°C. The time of the reaction is not critical, but it is preferred that the reaction be run for 2 to 30 hours, preferably 10 to 20 hours. The product is recovered by conventional techniques, e.g., extraction and evaporation.

The compound of formula (VII) and many of the compounds of formulas (II) in which $R_2$ is other than phenalkyl, (III), (IV) and (VI) are known and can be prepared by methods described in the literature. The compounds of formula (II) in which $R_2$ is other than phenalkyl, (III), (IV), and (VI) not specifically disclosed in the prior art can be prepared by analogous methods from known starting materials.

As previously indicated, the compounds of formula (I) are useful because they possess pharmacological activity in animals. In particular, the compounds are useful as anti-obesity agents as indicated by glucose transport tests carried out on male Wistar rats which are dosed orally with 20–80 milligrams per kilogram of body weight of the test compound after at least 20 hours of fasting. One hour after receiving the drug each animal is sacrificed and the upper small intestine is removed and washed with glucose-saline. A 5 cm. section of the intestine is everted so that the mucosal surface is on the outside. One end of the segment is tied off and the center of the sac so formed is filled with oxygen saturated Kreb's biocarbonate buffer. The other end is then closed and the sac is incubated in 10 ml. of oxygen saturated bicarbonate buffer for 60 minutes at 37°C. Both the outside and inside solutions contain initially 0.3% of glucose. At the end of the incubation time, the glucose content of the outer (mucosal) and the inner (serosal) solution is determined using the standard Autoanalyzer procedure. Similar tests are run simultaneously with control animals. The percent inhibition of glucose transport caused by the drug is calculated from the formula:

$$I = \frac{S_t - M_t}{S_c - M_c} \times 100$$

where
I = percent inhibition;
$S_t$ = glucose concentration (mg.%) of serosal fluid at the end of an experiment in the drug-treated animal;
$S_c$ = glucose concentration (mg.%) of serosal fluid at the end of an experiment in the control animal;
$M_t$ = glucose concentration (mg.%) of mucosal fluid at the end of an experiment in the drug treated animal
$M_c$ = glucose concentration (mg.%) of mucosal fluid at the end of an experiment in the control animal.

The compounds of the formula I are also useful because they possess hypolipidemic activity in animals. More particularly, the compounds of formula I are useful as hypolipidemic agents as indicated by the fall in cholsterol and triglyceride levels in male albino Wistar rats weighing 110–130 g. initially. The rats are maintained on drug-free laboratory chow diet for seven days and then divided into groups of 8 to 10 animals. Each group with the exception of the control is then given orally 0.06% to 0.25% in the feed diet of the compound for six days. At the end of this period, the animals are anesthetized with sodium hexobarbital and bled from the carotid arteries. Serum or plasma samples are collected and 1.0 ml of the serum is added to 9.0 ml redistilled isopropanol. Two autoanalyzer cupsful of a mixture of zeolite-copper hydroxide and Lloydds reagent (Kersler, G., and Lederer, H., 1965, Technicon Symposium, Madiad Inc., New York 345–347) are added, and the mixture is shaken for 1 hour. Cholesterol and triclyceride levels are determined simultaneously on the same sample by Technicon N24A (cholesterol) and N-78 (triglyceride) methodology. The mean total serum cholesterol levels are then computed and the hypocholesterolemic activity is expressed as the fall in cholesterol levels as a percentage of the control level. The change in serum triglyceride levels induced by the drug is computed as a percentage of the control tryglyceride levels.

For such usages, compounds (I) may be administered orally or perenterally as such or admixed with conventional pharmaceutical carriers. They may be administered orally in such forms as tablets, dispersible powders, granules, capsules, syrups, and elixirs, and parenterally as solutions, suspensions, dispersions, emulsions, and the like, e.g., a sterile injectable aqueous suspension. These pharmaceutical preparations may contain up to about 90% of the active ingredient in combination with the carrier or adjuvant.

Furthermore, these compounds of formula (I) may be similarly administered in the form of their non-toxic pharmaceutically acceptable acid addition salts. Such salts possess the same order of activity as the free base, are readily prepared by reacting the base with an appropriate acid and, accordingly, are included within the scope of the invention. Representative of such salts are the mineral acid salts, such as the hydrochloride, hydrobromide, sulfate, phosphate and the like and the organic acid salts, such as the succinate, benzoate, acetate, p-toluenesulfonate, benzene-sulfonate, maleate, malate, tartrate, methanesulfonate, cyclohexylsulfamate and the like.

The anti-obesity or hypolipidemic effective dosage of active ingrdedient employed for the treatment of obesity or lipidemia will vary depending on the particular compound employed and the severity of the condition being treated. However, in general, satisfactory results are obtained for both utilities when the compounds (I) are administered at a daily dosage of from about 0.5 milligrams to about 250 milligrams per kilogram of animal body weight, preferably given in divided doses 2 to 4 times a day, or in sustained release form. For most large mammals in need of said treatment, the total daily dosage is from 30 to about 1500 milligrams. Dosage forms suitable for internal use comprise from about 7.5 to about 750 milligrams of the active compound in intimate admixture with a solid or liquid pharmaceutically acceptable carrier or diluent.

The preferred pharmaceutical compositions from the standpoint of preparation and ease of administration are solid compositions, particularly hard-filled capsules and tablets containing about 25 to 100 milligrams of active ingredient.

Tablets and capsules containing the ingredients indicated below may be prepared by conventional techniques and are useful in treating obesity or lipidemia at a dose of one tablet or capsule 2 to 4 times a day.

| Ingredients | Weight (mg) tablet | capsule |
|---|---|---|
| N(3-isopropoxypropyl)-N'-(2-octyl)-p-phenylenediamine dihydrochloride | 50 | 50 |
| Tragacanth | 10 | — |
| Lactose | 197.5 | 250 |
| Corn Starch | 25 | |
| Talcum | 15 | |
| Magnesium Stearate | 2.5 | |

Similar tablets and capsules are prepared using N-(2-phenylethyl)-N'-(2-octyl)-p-phenylenediamine dihydrochloride in place of the N-(3-isopropoxypropyl)-N'-(2-octyl)-p-phenylenediamine dihydrochloride in the above formulations.

The following pharmaceutical compositions are formulated with the indicated amount of active agent using conventional techniques. The injectable suspension and the oral liquid suspension represent formulations useful as unit doses and may be administered in the treatment of obesity or lipidemia. The injectable suspension is suitable for administration once a day whereas the oral liquid suspension is suitably administered two to four times per day for this purpose.

| Ingredients | Weight (mg) sterile injectable suspension | oral liquid suspension |
| --- | --- | --- |
| N-(isopropoxypropyl)-N'-(2-octyl)-p-phenylenediamine dihydrochloride | 50 | 50 |
| sodium carboxy methyl cellulose USP | 1.25 | 12.5 |
| methyl cellulose | 0.4 | — |
| polyvinylpyrrolidone | 5 | — |
| lecithin | 3 | — |
| benzyl alcohol | 0.01 | — |
| magnesium aluminum silicate | — | 47.5 |
| flavor | — | q.s. |
| color | — | q.s. |
| methyl paraben, USP | — | 4.5 |
| propyl paraben, USP | — | 1.0 |
| polysorbate 80 (e.g. Tween 80), USP | — | 5 |
| sorbitol solution, 70% USP | — | 2,500 |
| buffer agent to adjust pH for desired stability | q.s. | q.s. |
| water | for injecton q.s. to 1 ml. | to 5 ml. |

Injectable suspensions and oral liquid suspensions are similarly prepared using N-(2-phenylethyl)-N'-(2-octyl)-p-phenylenediamine dihydrochloride in place of the N-(3-isopropoxypropyl)-N'-(2-octyl)-p-phenylenediamine dihydrochloride above.

EXAMPLE I

N-(3-Isopropoxypropyl)-N'-(2-octyl)-p-phenylenediamine

A mixture of 20 g. of N-(3-ispropoxypropyl)-p-phenylenediamine, 14 g. of 2-octanone and 0.3 g. of 5% platinum sulfide-on-carbon catalyst is shaken in a rocker bomb at 150° under 600 psi hydrogen for 5 hours. After allowing the mixture to cool to room temperature, the contents of the bomb are dissolved in methanol and filtered through celite. The filtrate is evaporated in vacuo and the residue is taken up in ether and treated with an excess of dry hydrogen chloride gas. The resultant solid is collected by filtration and recrystallized from methanol-acetone to yield the product N-(3-isopropoxypropyl)-N'-(2-octyl)-p-phenylenediamine dihydrocloride (m.p. 200°–202°C.).

When an equivalent amount of 2-heptanone, 2-decanone or 2-undecanone is used in place of the 2-octanone above, there is obtained the dihydrochloride salt of N-(3-isopropoxypropyl)-N'-(2-heptyl)-p-phenylenediamine (m.p. 215°–217°C) N-(3-ispropoxypropyl)-N'-(2-decyl)-p-phenylenediamine (m.p. 204°–206°C) or N-(3-isopropoxypropyl)-N'-(2-undecyl)-p-phenylenediamine., (m.p. 204°–206°C), respectively.

When the above process is carried out using an equivalent amount of N-(3-methoxypropyl)-p-phenylenediamine, N-[2-(n-butoxy) ethyl]p-phenylenediamine, N-(3-ethoxypropyl)-p-phenylenediamine, N-[3-(1-methylpropoxy)propyl]-p-phenylenediamine, or N-[3-(n-propoxy)propyl]-p-phenylenediamine in place of N-(3-isopropoxypropyl)-p-phenylenediamine above, there is obtained N-(3-methoxypropyl)-N'-(2-octyl)-p-phenylenediamine (m.p. in dihydrochloride salt form, 56°–58°C), N-[2-(n-butoxy)ethyl]-N'-(2-octyl)-p-phenylenediamine (m.p. on dihydrochloride salt form, 192°–195°C), N-(3-ethoxypropyl)-N'-(2-octyl)-p-phenylenediamine (m.p. in dihydrochloride salt form, 191°–193°C), N-[3-(1-methylpropoxy)propyl]-N'-(2-octyl)-p-phenylenediamine (m.p. in dihydrochloride salt form, 209°–211°C) or N-[3-(n-propoxy)propyl]-N'-(2-octyl)-p-phenylenediamine (mp in dihydrochloride salt form, 208°–210°C), respectively.

EXAMPLE 2

N-(2-Phenylethyl)-N'-(2-(2-octyl)-p-phenylenediamine

Step A: N-(2-phenylethyl)-p-nitroaniline

A mixture of 50 g. of 1-chloro-4-nitrobenzene, 76 g. of 2-phenylethylamine, and 30 ml. of dimethylsulfoxide is heated for 18 hours at 150°C. The resultant reaction mixture is poured into 3 liters of water. The precipitate formed is recovered by filtration and recrystallized from ether to yield the product, N-(2-phenylethyl)-p-nitroaniline; m.p. 57°–59°C.

Step B: N-(2-phenylethyl)-p-phenylenediamine

A mixture of 15 g. of N-(2-phenylethyl)-p-nitroaniline, 100 ml. of methanol, and 2.5 g. of 10% palladium on carbon catalyst is shaken under 1 to 2 atmospheres of hydrogen until uptake of the hydrogen ceases. The resultant reaction mixture is filtered through celite and washed with methanol. The filtrate is concentrated in vacuo to yield the product, N-(2-phenylethyl)-p-phenylenediamine, as an oil which can be converted to the dihydrochloride, m.p. 247°C. by bubbling hydrogen chloride gas through a solution of the oil in ether for ½ hour.

Step C: N-(2-phenylethyl)-N'-(2-octyl)-p-phenylenediamine

A mixture of 20 g. of N-(2-phenylethyl)-p-phenylenediamine, 13.8 g. of 2-octanone and 0.2 g. of 5% platinum sulfide-on-carbon catalyst is shaken in a rocker bomb at 150° under 600 psi hydrogen for 4 hours. After allowing the mixture to cool to room temperature, the contents of the bomb are dissolved in methanol and filtered through celite. The filtrate is evaporated in vacuo and the residue is taken up in ether and treated with an excess of dry hydrogen chloride gas. The resultant solid is collected by filtration and recrystallized from methanol-acetone to yield the product N-(2-phenylethyl)-N'-(2-octyl)-p-phenylenediamine dihydrochloride (m.p. 198°–203°C.)

When an equivalent amount of 2-heptanone, 2-decanone or 2-undecanone is used in place of the 2-octanone above, there is obtained N-(2-phenylether)-N'-

(2-heptyl)-p-phenylenediamine, or N-(2-phenethyl)-N'-(2-decyl)-p-phenylenediamine, or N-(2-phenylethyl)-N'-(2-undecyl)-p-phenylenediamine, respectively.

Following the procedures of steps A, B, and C and using an equivalent amount of 3-phenylpropylamine or 4-phenylbutylamine in place of the 2-phenylethylamine used in Step A, there is obtained, after reduction to the corresponding p-phenylenediamine, reductive alkylation with 2-octanone and treatment with hydrogen chloride gas, the dihydrochloride salt of N-(3-phenylpropyl)-N-(2-octyl)-p-phenylenediamine (m.p. 220°–225°C) or N-(4-phenylbutyl)-N'-(2-ocytl)-p-phenylenediamine (m.p. 215°–222°C) respectively.

EXAMPLE 3

N-(3-Isopropoxypropyl)-N'-(2-octyl)-p-phenylenediamine

A mixture of 20 g. of N-(2-octyl)-p-phenylenediamine, 14 g. of 3-isopropoxypropionaldehyde and 0.3g. of 5% platinum sulfide on carbon catalyzt is shaken in a rocker bomb at 150°C under 600 psi hydrogen for 5 hours. After allowing the mixture to cool to room temperature, the contents of the bomb are dissolved in methanol and filtered through celite. The filtrate is evaporated in vacuo and the residue is taken up in ether and treated with an excess of dry hydrogen chloride gas. The resulant solid is collected by filtration and recrystallized from methanol-acetone to yield the product N-(3-isopropoxypropyl)-N'-(2-octyl)-p-phenylenediamine in dihydrochloride salt form (mp 200°–202°C).

When an equivalent amount of 2-phenylacetaldehyde is used in place of the 3-isopropoxypropionaldehyde above, there is obtained N-(2-phenylethyl)-N'-(2-octyl)-p-phenylenediamine in dihyrochloride salt form (mp 198°–203°C.).

EXAMPLE 4

N-(3-isopropoxypropyl)-N'-(2-octyl)-p-phenylenediamine

A mixture of 50 g. of N-(3-isopropoxypropyl)-p-phenylenediamine, 50 g. of 2-octyl bromide, 200 ml. of 2N sodium carbonate and 1 liter of ethanol is stirred for 18 hours at 60°C. The reaction mixture is treated with 1 liter of water and extracted with 1 liter of ether. The ether layer is separated, washed with 1200 ml. of water, dried over sodium sulfate and evaporated in vacuo. A mixture of the residue in ether is treated with hydrogen chloride gas to yield the title product in dihydrochloride salt form, m.p. 200°–202°C.

When the above process is carried out using an equivalent amount of 2-heptyl bromide, 2-decyl bromide or 2-undecyl bromide in place of the 2-octyl bromide, there is obtained the dihydrochloride salt of N-(3-isopropoxypropyl)-N'-(2-heptyl)-p-phenylenediamine (m.p. 215°–217°C.), N-(3-isopropoxypropyl)-N'-(2-decyl)-p-phenylenediamine (m.p. 204°–206°C) or N-(3-isopropoxypropyl)-N'-(2-undecyl)-p-phenylenediamine (m.p. 204°–206°C), respectively.

Following the above procedure, but using an equivalent amount of N-(2-methoxypropyl)-p-phenylenediamine, N-[2-(n-butoxy)ethyl]-p-phenylenediamine, N-(3-ethoxypropyl)-p-phenylenediamine, N-[3-(1-methylpropoxy) propyl]-p-phenylenediamine or N-[3-(n-propoxy)propyl]-p-phenylenediamine in place of the N-(3-isopropoxypropyl)-p-phenylenediamine, there is obtained the dihydrochloride salt of N-(3-methoxypropyl-N'-(2-octyl)-p-phenylenediamine (m.p. 56°–58°C), N-[3-(n-butoxy)ethyl]-N'-(2-octyl)-p-phenylenediamine (m.p. 192°–195°C), N-(3-ethoxypropyl)-N'-(2-octyl)-p-phenylenediamine (m.p. 191°–193°C), N-[3(1-methylpropoxy)propyl]-N'-(2-octyl)-p-phenylenediamine (m.p. 209°–211°C) or N-[3-(n-propoxy)propyl]-N'-(2-octyl)-p-phenylenediamine (m.p. 208°–210°C), respectively.

EXAMPLE 5

N-(2-phenylethyl-N'-(2-octyl)-p-phenylenediamine

Following essentially the same procedure as in Example 4, but using an equivalent amount of N-(2-phenylethyl)-p-phenylenediamine (prepared as in Example 2b) in place of the N-(3-isopropoxypropyl)-p-phenylenediamine, and carrying out the reaction at 70°C, there is obtained N-(2-phenylethyl)-N'-(2-octyl)-p-phenylenediamine dihydrochloride (m.p. 198°–203°C).

When the procedure of example 4 is carried out at 70°C using an equivalent amount of N-(3-phenylpropyl)-p-phenylenediamine or N-(4-phenylbutyl)-p-phenylenediamine in place of the N-(3-isopropoxypropyl)-p-phenylenediamine there is obtained N-(3-phenylpropyl)-N'-(2-octyl)-p-phenylenediamine dihydrochloride (m.p. 220°–225°C) or N-(4-phenylbutyl)-N'-(2-octyl)-p-phenylenediamine dihydrochloride, (m.p. 215°–222°C).

EXAMPLE 6

N-(3-isopropoxypropyl)-N'-(2-octyl)-p-phenylenediamine

Following the same conditions as in Example 4, but reacting N-(2-octyl)-p-phenylenediamine with 3-isopropoxypropyl bromide, there is obtained the title product in dihydrochloride salt form (m.p. 200°–202°C).

In a similar manner, reacting N-(2-octyl)-p-phenylenediamine with 1-bromo-2-phenylethane, there is obtained N-(2-phenethyl)-N'-(2-octyl)-p-phenylenediamine, dihydrochloride (m.p. 198°–203°C).

What is claimed is:

1. A compound of the formula

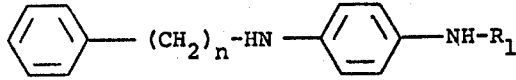

where
 n is 2, 3, or 4, and
 $R_1$ is a straight or branched chain alkyl having 5 to 11 carbon atoms,
or a pharmaceutically acceptable acid addition salt thereof.

2. The compound of claim 1 which is N-(2-phenylethyl)-N'-(2-octyl)-p-phenylenediamine.

3. The compound of claim 1 which is N-(3-phenylpropyl)-N'-(2-octyl)-p-phenylenediamine.

4. The compound of claim 1 which is N-(4-phenylbutyl)-N'-(2-octyl)-p-phenylenediamine.

* * * * *